(12) United States Patent
Michels et al.

(10) Patent No.: US 6,890,295 B2
(45) Date of Patent: May 10, 2005

(54) ANATOMICAL SPACE ACCESS TOOLS AND METHODS

(75) Inventors: Koen Michels, Maastricht (NL); Nicolaas Lokhoff, Kerkrade (NL); Matthew D. Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 46 days.

(21) Appl. No.: 10/284,771

(22) Filed: Oct. 31, 2002

(65) Prior Publication Data

US 2004/0087831 A1 May 6, 2004

(51) Int. Cl.⁷ .............................................. A61B 1/00
(52) U.S. Cl. ...................... 600/114; 600/37; 600/204
(58) Field of Search .................................. 604/117, 115, 604/506, 93.01, 164.4, 176, 902, 96.01, 264, 528, 908; 606/205, 167, 108; 600/508, 374, 509, 564, 114, 115, 201, 204, 205, 210

(56) References Cited

U.S. PATENT DOCUMENTS

| | | | |
|---|---|---|---|
| 4,723,940 A | * 2/1988 | Wiegerinck | 604/115 |
| 4,991,578 A | 2/1991 | Cohen | 128/419 |
| 5,336,252 A | 8/1994 | Cohen | 607/119 |
| 5,402,772 A | 4/1995 | Moll et al. | 128/20 |
| 5,452,733 A | 9/1995 | Sterman et al. | 128/898 |
| 5,464,447 A | 11/1995 | Fogarty et al. | 607/129 |
| 5,716,392 A | 2/1998 | Bourgeois et al. | 607/132 |
| 5,827,216 A | 10/1998 | Igo et al. | 604/21 |
| 5,836,311 A | 11/1998 | Borst et al. | |
| 5,868,770 A | 2/1999 | Rygaard | 606/167 |
| 5,875,782 A | 3/1999 | Ferrari et al. | 128/898 |
| 5,931,810 A | 8/1999 | Grabek | 604/51 |
| 5,972,013 A | 10/1999 | Schmidt | 606/185 |
| 6,015,378 A | 1/2000 | Borst et al. | |
| 6,080,175 A | 6/2000 | Hogendijk | 606/185 |
| 6,156,009 A | 12/2000 | Grabek | 604/117 |
| 6,162,195 A | 12/2000 | Igo et al. | 604/164 |
| 6,206,004 B1 | 3/2001 | Schmidt et al. | 128/898 |
| 6,231,518 B1 | 5/2001 | Grabek et al. | 600/508 |
| 6,328,688 B1 | 12/2001 | Borst et al. | |
| 6,332,468 B1 | 12/2001 | Benetti | 128/898 |
| 6,334,843 B1 | 1/2002 | Borst et al. | |
| 6,336,898 B1 | 1/2002 | Borst et al. | |
| 6,350,229 B1 | 2/2002 | Borst et al. | |
| 6,364,826 B1 | 4/2002 | Borst et al. | |
| 6,371,906 B1 | 4/2002 | Borst et al. | |
| 6,394,948 B1 | 5/2002 | Borst et al. | |
| 6,423,051 B1 | 7/2002 | Kaplan et al. | 604/506 |
| 6,440,061 B1 | * 8/2002 | Wenner et al. | 600/114 |
| 6,464,630 B1 | * 10/2002 | Borst et al. | 600/37 |
| 6,558,382 B2 | 5/2003 | Jahns et al. | |

(Continued)

Primary Examiner—Beverly M. Flanagan
(74) Attorney, Agent, or Firm—Jeffrey J. Hohenshell; Tom Berry

(57) ABSTRACT

Medical devices and methods for accessing an anatomical space of the body and particularly for penetrating the epicardium to access pericardial space and the epicardial surface of the heart in a minimally invasive manner employing suction are disclosed. The distal end of a tubular access sleeve having a sleeve wall surrounding a sleeve access lumen and extending between a sleeve proximal end and a sleeve distal end having a plurality of suction ports arrayed around the sleeve access lumen distal end opening is applied against an outer tissue layer. Suction is applied through the plurality of suction ports to a plurality of portions of the outer tissue layer. A perforation instrument is introduced through the sleeve access lumen to perforate the outer tissue layer to form an access perforation into the anatomic space while the applied suction stabilizes the outer tissue layer, whereby further treatment drugs and devices can be introduced into the anatomic space.

33 Claims, 7 Drawing Sheets

U.S. PATENT DOCUMENTS

| | | |
|---|---|---|
| 6,605,037 B1 * | 8/2003 | Moll et al. .................. 600/204 |
| 6,755,780 B2 | 6/2004 | Borst et al. |
| 2002/0002372 A1 | 1/2002 | Jahns et al. |
| 2002/0120177 A1 | 8/2002 | Borst et al. |
| 2002/0124856 A1 | 9/2002 | Borst et al. |
| 2003/0078470 A1 | 4/2003 | Borst et al. |
| 2003/0078575 A1 | 4/2003 | Jahns et al. |

* cited by examiner

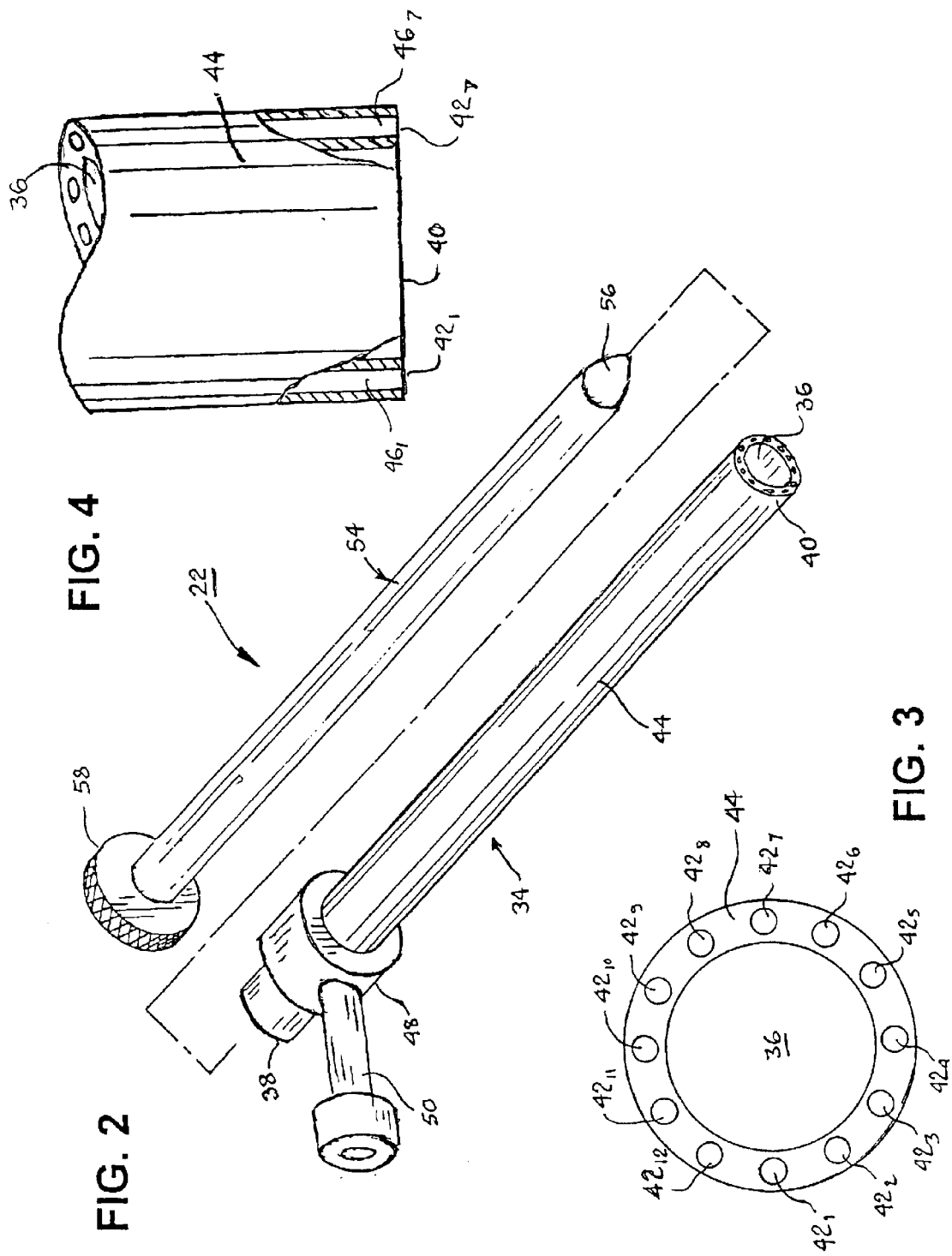

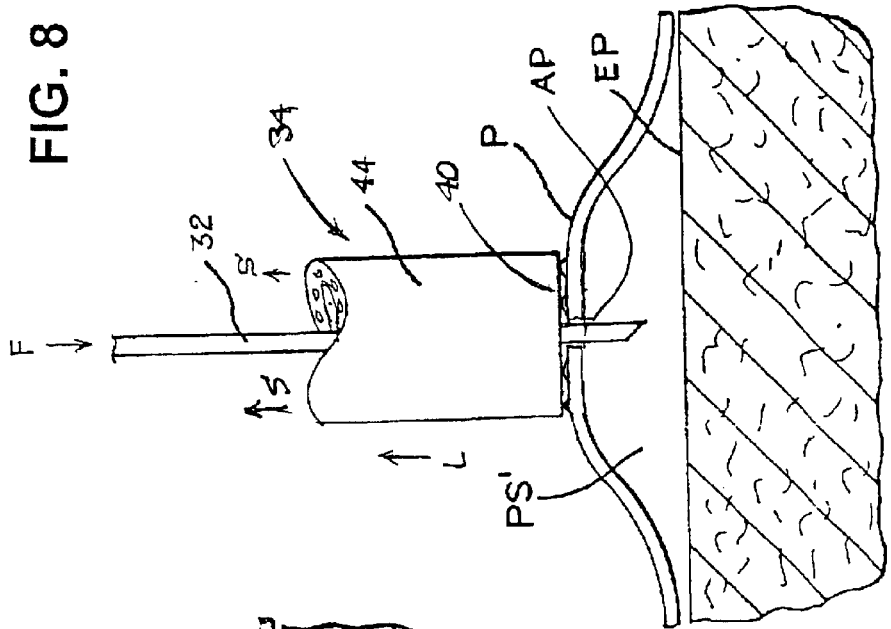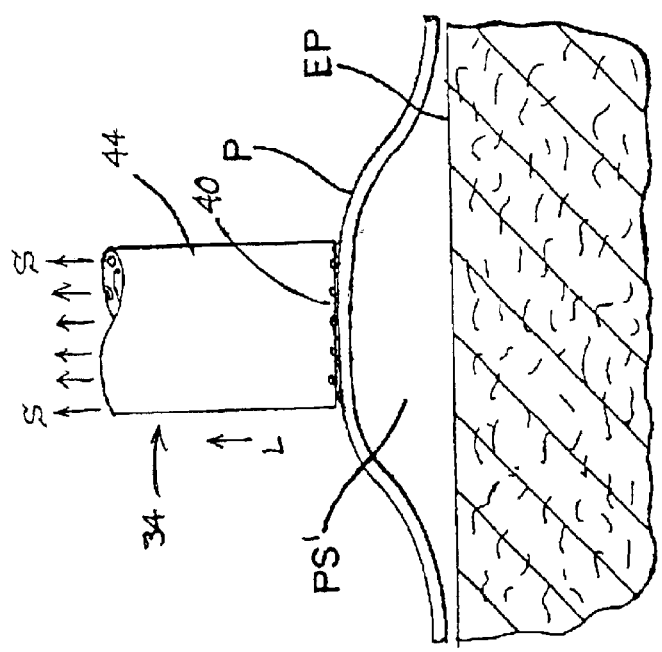

ANATOMICAL SPACE ACCESS TOOLS AND METHODS

FIELD OF THE INVENTION

The present invention pertains to medical devices and methods for accessing an anatomical space of the body and particularly for entering the epicardium to access pericardial space and the epicardial surface of the heart in a minimally invasive manner.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

It is frequently medically necessary to access the pericardial space to treat an injury, infection, disease or defect of the heart, e.g., an occluded coronary artery, a defective heart valve, aberrant electrical pathways causing tachyarrhythmias, bacterial infections, to provide cardiac resynchronization therapy, or to place epicardial pacing or cardioversion/defibrillation electrodes against the epicardium or into the myocardium at selected sites. It is necessary in these procedures to surgically expose and cut through the pericardium to obtain access to the pericardial space.

Highly invasive surgical techniques, referred to as a median sternotomy (open-chest surgical exposure) or a thoracotomy, have been typically employed to provide the surgeon access to the pericardial space and the heart. A median sternotomy incision begins just below the sternal notch and extends slightly below the xyphoid process. A sternal retractor is used to separate the sternal edges for optimal exposure of the heart. Hemostasis of the sternal edges is typically obtained using electrocautery with a ball-tip electrode and a thin layer of bone wax.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Postoperatively, most patients endure significant pain and must forego work or strenuous activity for a long recovery period.

Many minimally invasive surgical techniques and devices have been introduced In order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in U.S. Pat. Nos. 6,332,468, 5,464,447, and 5,716,392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the sleeve or port in place. Surgical instruments and other devices such as fiber optic thoracoscopes can be inserted into the body cavity through the sleeve or port lumens. As stated in the '468 patent, instruments advanced through trocars can include electrosurgical tools, graspers, forceps, scalpels, electrocauteries, clip appliers, scissors, etc.

In such procedures, the surgeon can stop the heart by utilizing a series of internal catheters to stop blood flow through the aorta and to administer cardioplegia solution. The endoscopic approach utilizes groin cannulation to establish cardio-pulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures eliminate the need for any form of CPB, the extensive surgical procedures necessary to connect the patient to a CPB machine, and to stop the heart. These beating heart procedures can be performed on a heart exposed in a full or limited thoracotomy or accessed percutaneously.

In such percutaneous procedures, the epicardium of the beating or stopped heart is exposed to view typically by use of grasping and cutting instruments inserted through one port to cut through the pericardium surrounding the heart while the area is viewed through the thoracoscope or endoscope inserted through another port. The thoracoscopic approach typically requires the placement of a chest tube and admission to the hospital for the initial 1–2 post-operative days.

Therefore, much effort has been expended to develop medical devices and techniques to access the pericardial space employing such minimally invasive percutaneous procedures. One difficulty has been that normally the pericardial space is so small or thin that it is difficult to penetrate the pericardium using miniaturized instruments capable of being introduced through a port to the site without also puncturing the underling epicardium and thereby, damaging the myocardium or a coronary vessel. Proliferative adhesions occur between the pericardium and the epicardium in diseased hearts and hamper access to the pericardial space employing such minimally invasive percutaneous procedures. The simple percutaneous approach can be used to penetrate the pericardium to drain a large pericardial effusion, i.e., an accumulation of too much fluid in the pericardial space that widens the pericardial space. A spinal needle (18–20 gauge) and stylet occluding the needle lumen are advanced incrementally in a superior/posterior fashion through a small (2–4 mm) cutaneous incision between the xyphoid and costal cartilage. Periodically, the stylet is removed, and fluid aspiration is attempted through the needle lumen. The advancement is halted when fluid is successfully aspirated, and the pericardial effusion is then relieved.

Methods and apparatus for accessing the pericardial space for the insertion of implantable defibrillation leads are disclosed in U.S. Pat. Nos. 5,071,428 and 6,156,009, wherein a forceps device is used to grip the pericardium and pull it outward to form a "tent". In the '428 patent, a scissors or scalpel is introduced to cut the pericardium (pericardiotomy) under direct vision through a sub-xyphoid surgical incision. The forceps device disclosed in the '009 patent incorporates a mechanism for introducing electrical leads or guidewires through the outwardly displaced pericardium. It is difficult to introduce and use the forceps through the narrow lumen of a port or sleeve, particularly if the pericardial fluid is under pressure that makes the pericardium taut like an inflated balloon.

Further methods and apparatus for accessing the pericardial space for the insertion of devices or drugs are disclosed in U.S. Pat. No. 6,423,051, wherein an access tube having a device access lumen is provided with a plurality of hooks in the tube distal end that can be used to hook into the pericardium to enable the lifting and "tenting" of the pericardium. A cutting instrument or sharpened tip guidewire or the like can be advanced through the device access lumen to perforate the pericardium.

Other methods and apparatus that are introduced through percutaneously placed ports or directly through small transthoracic incisions for accessing the pericardial space employ suction devices to grip the epicardium as disclosed, for example, in U.S. Pat. Nos. 4,991,578, 5,336,252, 5,827,216, 5,868,770, 5,972,013, 6,080,175, and 6,231,518. The suction device is configured like a catheter or tube having a single suction lumen and typically having a further instrument delivery lumen. The suction lumen terminates in a single suction lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

For these reasons, it would be desirable to provide additional and improved methods and apparatus for the minimally invasive access to a patient's pericardial space. The methods and devices should be suitable for a wide variety of minimally invasive approaches to the pericardium, including at least intercostal/transthoracic and subxiphoid approaches, and the like. The methods and devices should further provide for secure and stable capture of the pericardium and permit the opening of a large space or volume between the pericardium and epicardium. Such access methods and apparatus should be useful for a wide variety of procedures to be performed in the pericardial space, including fluid withdrawal, drug delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like. At least some of these objectives will be met by the invention described herein.

SUMMARY OF THE INVENTION

The present invention provides methods, apparatus, and kits for accessing an anatomic space between an inner tissue layer and an outer tissue layer. The phrase "anatomic space" is meant to include any natural, potential, or created space or cavity within a patient's body where it may be desirable to gain access for surgical, diagnostic, therapeutic, lead delivery, visualization, or any other purpose. The inner tissue layer may consist of a membrane, a capsule or the adventia, muscularis and endothelial layers of a hollow organ or vessel. The methods, apparatus, and kits are particularly useful for minimally invasive access procedures, but could also be used for accessing internal anatomic spaces where initial access to the outer tissue layer is achieved via open surgical procedures. The present invention will be particularly useful for accessing a patient's pericardial space between the epicardium and pericardium for performing a wide variety of procedures, generally as set forth above. Other internal organs that may be accessed include the intestines, fallopian tubes, gall bladder, kidneys, and the like.

Apparatus and methods according to the present invention for accessing an anatomic space between an accessible outer tissue layer and an inner tissue layer utilize suction applied to the outer tissue layer through a plurality of relatively small suction ports at the distal end of a tubular access sleeve, e.g., a trocar sleeve, applied against the outer tissue layer. The plurality of suction ports are formed in the distal end surface of the wall of the tubular access sleeve and are either flush with the end surface or extend slightly distal to the end surface. The suction ports are arrayed around the sleeve wall distal end and substantially surround a device access lumen of the sleeve. Each of the plurality of suction ports in the sleeve distal end communicates with a suction manifold through a plurality of suction lumens in the sleeve wall. The suction manifold can be coupled to a vacuum source. Alternatively, each suction lumen or groups of suction lumens can be coupled separately to a vacuum source through individual valves, so that the loss of suction at any given suction port does not affect the suction applied at other suction ports. The applied suction stabilizes a ring of the outer tissue layer, so that the outer tissue layer can be lifted away from the wall to increase the anatomic space by lifting the proximal end of the sleeve.

The plurality of suction ports arrayed around the sleeve distal end provide more robust fixation to the outer tissue layer than a single large area suction port due to their redundancy. At least some of the plurality of suction ports readily engage the tissue surface under low suction force to enable lifting of the outer tissue layer. Engagement of tissue surface areas by all of the suction ports is not necessary. Similarly, the loss of engagement of some of suction ports with the tissue surface areas does not result in complete loss of engagement as is the case when an edge of a single large suction port releases from the tissue surface of the outer tissue layer.

A perforation device, e.g., a knife, a needle, a stiff guidewire tip, an electrosurgical cutting tool or other piercing or cutting instrument, can then be introduced through the sleeve access lumen to perforate the outer tissue layer and form an access hole or perforation there through creating access into the anatomic space while the access tube stabilizes the outer tissue layer. Advantageously, there is no suction applied through the sleeve access lumen that is necessary to maintain the attachment to the outer tissue layer while it is being perforated or other instruments are advanced through the perforation. The fixation of the outer tissue layer is not lost when the outer tissue layer is perforated. Moreover, it is simpler to advance instruments through the sleeve access lumen from a proximal lumen end opening that is exposed to the atmosphere.

In a further aspect of the present invention, a retention mechanism is inserted through the sleeve access lumen and the created access hole through the outer tissue layer and deployed in the anatomic space to inhibit retraction of the sleeve distal end from contact against the outer surface of the outer tissue layer. Additionally, the retention mechanism can be incorporated into an access device or catheter inserted into the anatomic space and deployed to bear against the inner surface of the outer tissue layer.

The methods, apparatus and kits of the present invention can advantageously be used to access the pericardial space between the pericardium and epicardium. In a still further aspect of the present invention, various devices are introduced into the pericardial space for temporary treatment of the heart or pericardial space or to complete a surgical procedure or for permanent implantation against the epicardium or within the pericardial space or within the myocardium or within a coronary vein or artery.

The tubular access sleeve can be circular or oval or have any other desirable cross-section shape. The tubular access sleeve can be straight, curved for formed with a bend or formed of a bendable material to be shaped by the user.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is a perspective view of a trocar sleeve of the present invention associated with a trocar puncture rod that fits into the trocar sleeve lumen to form a trocar for making a percutaneous incision;

FIG. 3 is an expanded end view of the trocar sleeve distal end depicting a plurality of suction ports in the trocar sleeve distal end that are in communication with trocar sleeve lumens in the sleeve wall;

FIG. 4 is an expanded partial side view in partial cross-section of the trocar sleeve wall exposing suction ports in the trocar sleeve distal end in communication with trocar sleeve lumens in the sleeve wall;

FIG. 7 is a schematic illustration of the application of suction from the plurality of suction ports to the epicardium enabling lifting of the epicardium to expand the pericardial space;

FIG. 8 is a schematic illustration the insertion of a cutting instrument through the sleeve access lumen to perforate the pericardium during the application of suction from the plurality of suction ports to the epicardium enabling lifting of the epicardium to expand the pericardial space;

DETAILED DESCRIPTION OF THE PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for accessing the pericardial space between the epicardium and the pericardium as an example of accessing an anatomic space between an inner tissue layer and an outer tissue layer, respectively.

The access to the pericardial space in accordance with the present invention facilitates the performance of a number of ancillary procedures. For example, the procedures include introducing and locating the distal end of a catheter or guidewire or an electrode of a cardiac ablation catheter or a pacing lead or a cardioversion/defibrillation lead within the pericardial space and attached to the epicardium or myocardium. Other possible procedures include performing a coronary artery anastomosis in a thoracoscopic CABG procedure, replacing a defective heart valve, ablating aberrant electrical pathways in the atria to alleviate atrial tachyarrhythmias, introducing drugs or anti-bacterial agents into the pericardial space, relieving pericardial fluid pressure or providing cardiac resynchronization therapy.

The preferred embodiments of the present invention are incorporated into instruments referred to as "trocars" that are usually used to penetrate or be driven through tissue to form a wound or passage to an internal body organ or other structure. Such trocars are therefore elongated, tubular, and axially stiff and have a tissue penetrating distal end. Certain trocars are simply one-piece rods of a prescribed diameter and length that are advanced through tissue to form a passage and then removed so that other instruments can be advanced through the passage.

Other trocars comprise a tubular outer sleeve, sometimes referred to as a port or cannula or at times as the trocar itself, having a sleeve access lumen extending between lumen end openings at the sleeve proximal end and sleeve distal end, and an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece assembled trocar can be advanced as a unit through body tissue, and the inner puncture rod then removed leaving the trocar sleeve in place to maintain a fixed diameter passage through the tissue for use by other instruments.

Figure 1:
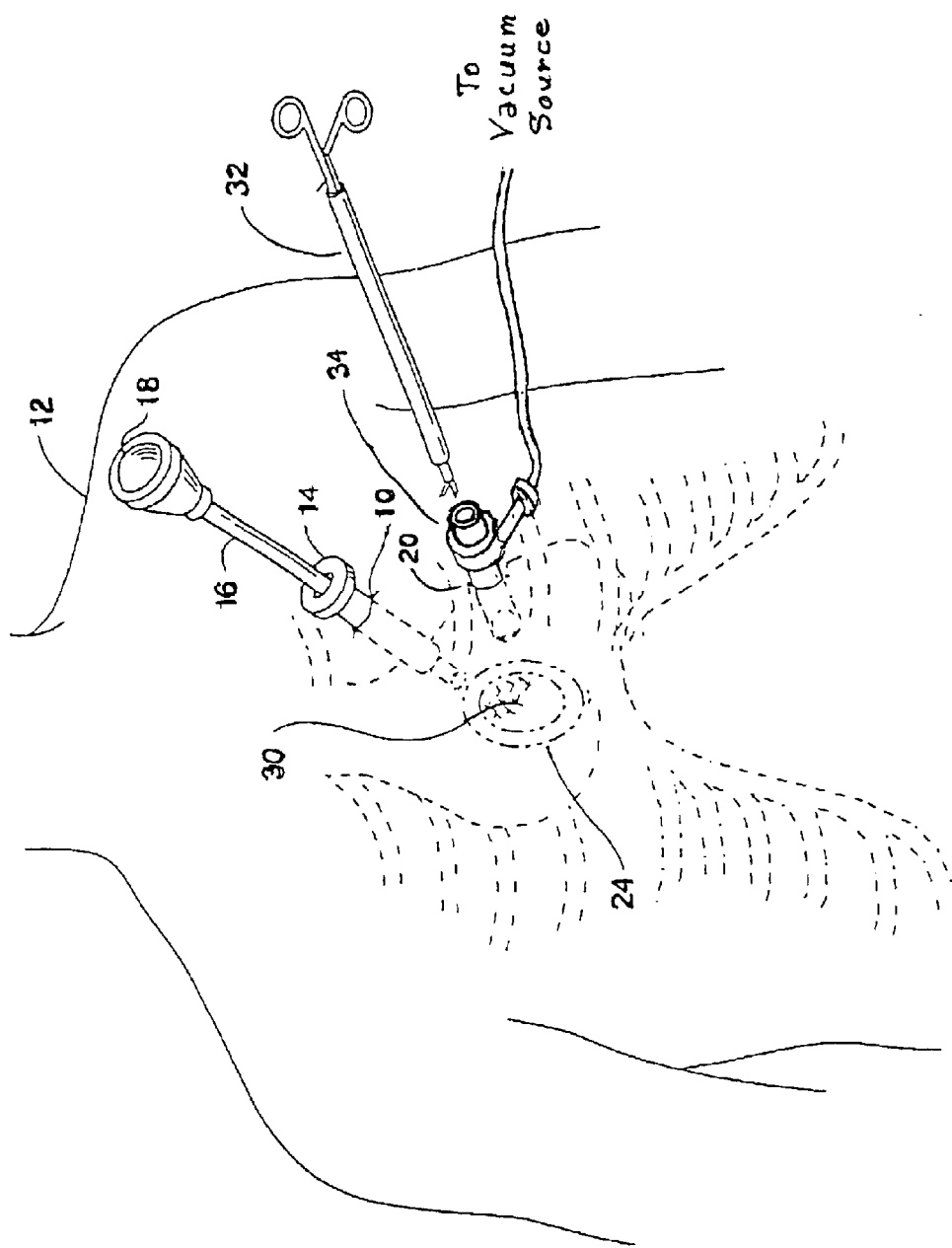
FIG. 1 is an illustration of the preparation of a patient for accessing the pericardial space through the use of a trocar sleeve of the present invention.

For example, FIG. 1 illustrates the placement of instruments for observation and accessing the pericardial space through an incision in the pericardium 24 exposing the heart 30 to perform any of the ancillary procedures listed above. The patient 12 is placed under general anesthesia, and the patient's left lung is deflated if necessary, using conventional techniques. The patient 12 is placed in a lateral decubitus position on his right side, and multiple small percutaneous incisions are to be made in the chest wall for the receipt of surgical instruments. As used herein, the term "percutaneous" refers to any penetration through the skin of the patient, whether in the form of a small cut, incision, hole, cannula, trocar sleeve or port or the like, that is preferably made in an interstitial space between the ribs of the patient.

A trocar sleeve 14 is shown left in place in a first passage 10 that is made as described above in the chest wall of a patient 12 between the patient's 2nd rib and 6th rib, for example. The selection of the exact location of the first passage 10 is dependent upon a patient's particular anatomy.

Typically, the patient's left lung is deflated by instruments advanced through the lumen of one of the trocar sleeves to allow unobstructed observation of the pericardium 24 employing a thoracoscope 16 inserted through the lumen of trocar sleeve 14. The deflation is accomplished by drawing a vacuum through a lung tube (not shown) that is inserted through the mouth or nose of the patient 12 into the left lung of the patient 12. After deflation, the peritoneal cavity is suffused with a gas, e.g., carbon monoxide, to pressurize the cavity to keep it open and sterile. The pressurized gas keeps the deflated lung away from the left heart so that the left heart can be viewed and accessed and provides a working space for the manipulation of the tools of the present invention.

The thoracoscope 16 is then inserted into the lumen of the trocar sleeve 14 to permit observation by a surgeon directly through an eyepiece 18 or indirectly through incorporation of a miniaturized image capture device, e.g., a digital camera, at the distal end of the thoracoscope 16 or optically coupled to the eyepiece 18 that is in turn coupled to an external video monitor (not shown). The thoracoscope 16 also incorporates a light source for illuminating the cavity with visible light so that the epicardial surface can be seen directly or indirectly. The depicted thoracoscope 16 is used to directly visualize the thoracic cavity and obtain a left lateral view of the pericardial sac or pericardium over the heart 30.

A two-piece trocar 22 of an embodiment of the present invention depicted in FIG. 2 is employed to make a second passageway 20 that is intercostal, i.e., between the ribs in this illustration, and the second trocar sleeve 34 is left in place as shown in FIG. 1. The second passageway 20 can be made in other locations in order to more readily access more cephalad and/or posterior sites of the left heart. The two-piece trocar 22 can be inserted in a sub-xyphoid approach or any other suitable approach through the chest wall, and the second trocar sleeve 34 left in place. A third passageway may be made using a further trocar for additional instrumentation or thoracoscopic observation or infusion of sterilizing gas as well as later placement of a chest drainage tube. Often, it will be advantageous to insert a fourth two-piece trocar for introducing a clipping or suturing device into the thoracic cavity through the lumen of the fourth trocar sleeve. In each case, the trocar rods are removed leaving the trocar sleeves in place.

The trocar 22 comprises the tubular outer trocar sleeve 34 and the puncture rod 54 that fits within the sleeve access lumen 36. The sleeve access lumen 36 is axially aligned with the elongated axis of the outer trocar sleeve 34 and extends between lumen end openings at the sleeve proximal end 38 and sleeve distal end 40. The puncture rod 54 extends between a proximal stop 58 and a tissue penetrating distal end 56 that extends distally from the sleeve distal end 40 when the puncture rod 54 is fitted into the sleeve access lumen 36 for use in making passageway 20. The two-piece assembled trocar 22 can be advanced as a unit through the chest wall between the ribs, and the puncture rod 54 can then removed leaving the trocar sleeve 34 in place to maintain a fixed diameter passage 20 through the chest wall for use by other instruments. The advancement of the trocar 22 as an assembly is carefully observed to ensure that the tissue penetrating distal end 56 is not advanced all of the way into contact with the pericardium 24.

In accordance with the present invention, the trocar sleeve 34 can then be advanced further into the passageway 20 to dispose the sleeve distal end 40 against the pericardium. The trocar sleeve 34 is configured to apply suction from a vacuum source, which can be a hospital operating room vacuum line or a simple hand operated vacuum pump or syringe, against the pericardium to grip and tent a portion of the pericardium 24 outward as the trocar sleeve is retracted proximally. The tenting is visualized by the surgeon through the thoracoscope 16. The parietal pleura is dissected and the pericardial sac is opened by instrument 32 introduced through the lumen of the second trocar sleeve 34.

The application of suction is accomplished through the incorporation of a plurality N of suction ports, e.g., twelve suction ports $42_1$–$42_{12}$, at the sleeve distal end 40 as shown in FIGS. 3 and 4. The suction ports $42_1$–$42_{12}$ at the sleeve distal end 40 communicate with a suction manifold 48 through at least one or a respective plurality of suction lumens, e.g., a like number of suction lumens $46_1$–$46_{12}$, in the sleeve wall 44. The suction lumens $46_1$–$46_{12}$ can extend the full distance between the suction manifold 48 and the suction ports $42_1$–$42_{12}$. Or the suction lumens $46_1$–$46_{12}$ can be joined together into a single lumen or combined into a lesser number of suction lumens at any point within or alongside the sleeve wall between the sleeve distal end 40 and the suction manifold 48. The manifold 48 can simply comprise an interior lumen within the sleeve wall or an enlargement of the sleeve wall that is coupled to the plurality of suction lumens $46_1$–$46_{12}$.

The suction ports $42_1$–$42_{12}$ are arrayed around the sleeve distal end 40 and substantially surround the sleeve access lumen 36 that is employed for device access into the pericardial space. A side port 50 extends laterally from the manifold 48 and has a standardized coupler for attachment with a vacuum source. It is expected that a relatively low suction provided by a pump or a manually operated syringe will suffice to enable lifting of the pericardium to expand the pericardial space beneath the sleeve distal end 40.

The trocar 22 is depicted as having a circular cross-section, but it will be understood that the trocar 22 can have a non-circular cross-section, e.g., an oval cross-section like the oval-shaped cardiac cannula disclosed in commonly assigned U.S. Pat. No. 6,146,371. Such an oval cross-section provides a minimum diameter enabling ready insertion between the patient's ribs and a maximum diameter that enlarges the area of the sleeve access lumen 36.

A distal section of the trocar sleeve wall 44 can be formed of a softer material than the proximal section of the sleeve wall 44 to prove a sleeve distal end 40 that can conform somewhat to the shape of the pericardium at a given site.

The sleeve distal end 40 can be at right angles to the axis of the sleeve wall 44 as depicted in FIG. 4. Or the sleeve distal end can be at a bevel or angle to the sleeve wall axis as shown, for example, by sleeve distal end 40' in FIG. 11 to facilitate the orientation of the sleeve distal end 40' to the pericardium when inserted between the ribs or in a sub-xyphoid approach toward the heart.

The number N of suction ports 42 can be selected as a function of the diameter of the sleeve 34 and the thickness of the sleeve wall 44 to optimize the function of lifting the pericardium around the sleeve access lumen 36. For example, it has been found that the number N of suction lumens 42 can number between 6 and 12.

Figure 5:
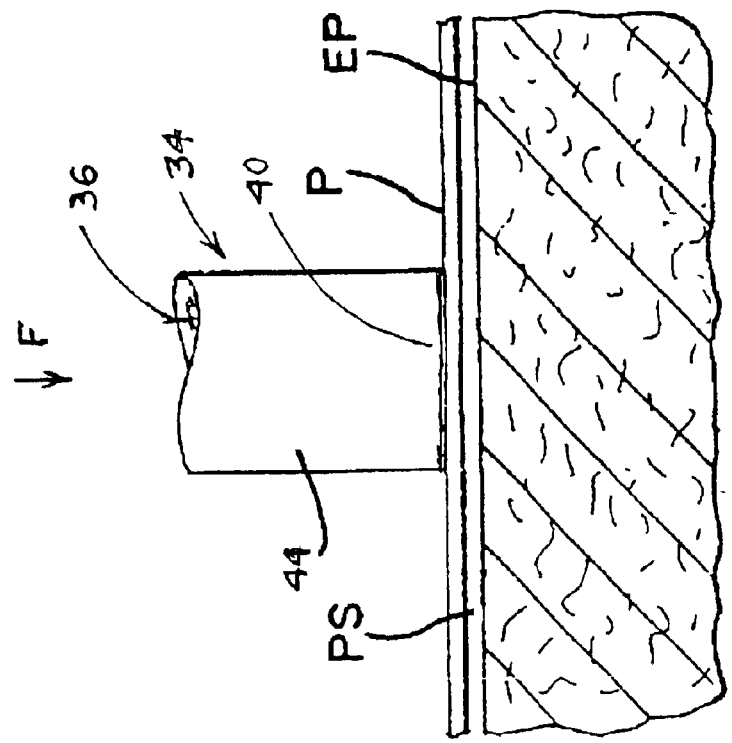
FIG. 5 is an expanded partial side view in partial cross-section of the trocar sleeve wall exposing suction ports in the trocar sleeve distal end in communication with trocar sleeve lumens in the sleeve wall wherein the suction ports extend distally from the trocar sleeve distal end to facilitate adherence to the pericardium.

Moreover, as illustrated in FIG. 5, it has been found desirable to extend the suction ports distally of the sleeve distal end 40 a few millimeters so as to facilitate drawing portions of the pericardium into the distal suction ports $42_1$–$42_8$ of the suction lumens $46_1$–$46_8$.

It will also be understood that a plurality of instruments can be introduced at the same time through the sleeve access lumen 36. In particular, a guidewire can be first advanced through the sleeve access lumen and into the pericardial space, and a further dilator, catheter, medical electrical lead, or other instrument can be introduced over the guidewire. The catheter can have a preformed curved tip or a deflectable tip so that the catheter distal end can be directed laterally within the pericardial space to enable lateral deployment of a wire or medical electrical lead or other instrument through the catheter lumen.

In addition, it may be desirable to insert a miniaturized, flexible, illumination and visualization endoscope through the sleeve access lumen 36 into the pericardial space to visually examine the pericardial space and track advancement or use of a catheter, medical electrical lead, or other instrument within the pericardial space.

Figure 6:
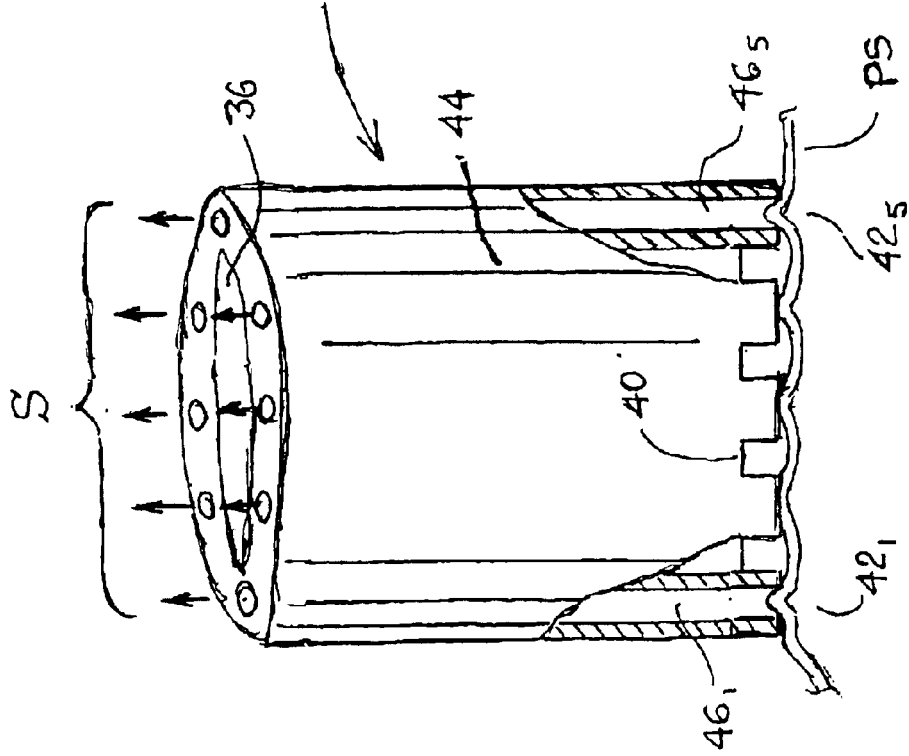
FIG. 6 is a schematic illustration of the advancement of the trocar sleeve distal end into contact with the epicardium of the heart of FIG. 1.

As illustrated in FIGS. 5–7, the applied suction (S) stabilizes at least N discrete portions of a ring of the outer tissue layer, i.e., the pericardium (P) in this exemplary embodiment, so that the outer tissue layer can be lifted away from the inner tissue layer, i.e., the epicardium (EP), by retracting or lifting the trocar sleeve proximal end 38 to increase the anatomic space, i.e., the pericardial space (PS). The increased pericardial space PS' is created by lifting the sleeve distal end 40 while the suction S grips the outer accessible surface of the pericardium as shown in FIG. 7. Then, a cutting or perforation instrument 32, e.g., a knife, scissors, a needle, a stiff guidewire tip, an electrosurgical cutting tool or other piercing instrument shown schematically in FIG. 8, can be introduced through the sleeve access lumen 36. The perforation instrument 32 is then used to perforate the pericardium P and form an access perforation (AP) therethrough of a sufficient size to enable access into the pericardial space PS' while the applied suction S continues to hold the pericardium P and enable enlargement of the pericardial space PS'.

Figure 9:
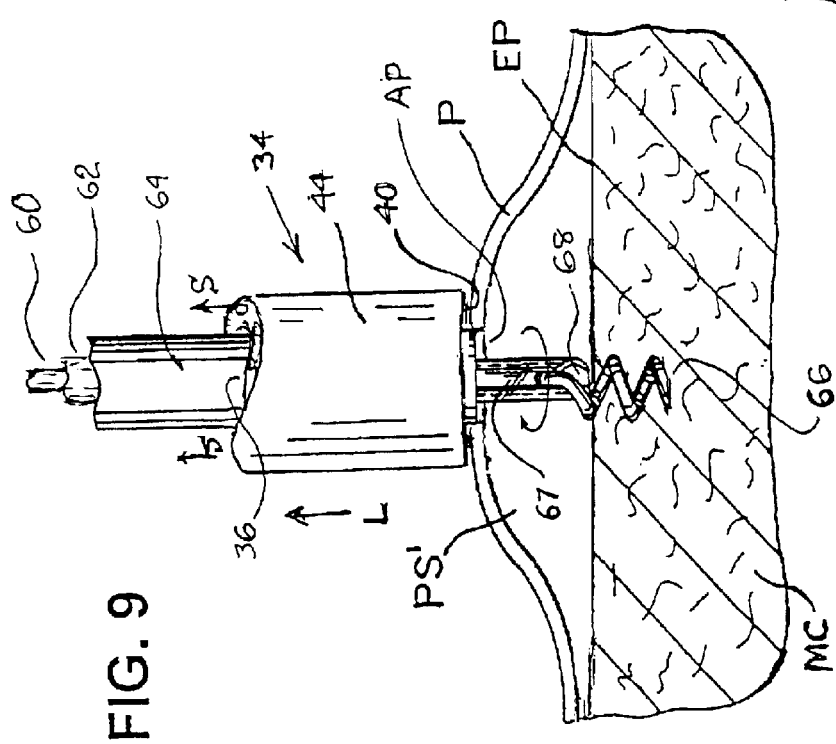
FIG. 9 is an illustration of the insertion of a cardiac pacing lead through the sleeve access lumen into the pericardial space during the application of suction from the plurality of suction ports to the epicardium enabling lifting of the epicardium to expand the pericardial space.

FIG. 9 is an illustration of the insertion of a cardiac pacing lead 60 through the sleeve access lumen 36 into the expanded pericardial space PS' during the application of suction S from the plurality of suction ports 42 to the epicardium EP enabling lifting of the epicardium EP to expand the pericardial space PS'. The cardiac pacing lead 60 can take any configuration, but the depicted configuration is a small diameter, straight conductor, highly flexible, screw-in epicardial lead having a fixation helix extending in axial alignment with the lead body axis similar to that depicted in commonly assigned U.S. Pat. No. 5,246,014, for example. It should be appreciated that the small diameter and high flexibility of the lead 60 render it too pliable for implantation without stiffening or confinement in an introducer. The lead 60 is therefore assembled into a system including an introducer 62 that fits over the lead body and a catheter 64 that fits over introducer 62 and lead 60. The inner diameter of the sleeve access lumen 36 is sufficiently large to receive the outer diameter of the catheter 64 when the assembly is inserted through it. The lead 60 terminates in a distal, electrically uninsulated, helical, screw-in electrode 66 electrically connected to the conductor of lead 60. It is expected that the assembly can be advanced laterally along the myocardium with minimal expansion of the pericardial space PS'.

As further illustrated in FIG. 9, the distal end 68 of the introducer 62 is shaped to engage the shank 67 of the helical screw-in electrode 66 so that it can be rotated by rotation of the proximal end of introducer 62 to screw the helical screw-in electrode 66 through the epicardium EP and into the myocardium (MC). In use, the trocar sleeve 34 is positioned as described above with respect to FIGS. 5–8 so that the applied suction S and lift L forms the expanded pericardial space PS'. The lead system is assembled by sliding the introducer 62 over the lead body until the distal end 68 of the introducer 62 firmly engages the screw-in electrode 66. Although it is depicted in FIG. 9, the outer catheter 64 may or may not be employed since the sleeve access lumen confines the introducer 62 and screw-in lead 60. The assembled lead system is inserted through the sleeve access lumen 36 so that the distal end 68 of the introducer 62 and screw-in electrode 66 are disposed through the access perforation AP and within the expanded pericardial space PS'. Rotational torque is imparted to the proximal end of the introducer 62 to screw the helical screw-in electrode 66 through the epicardium EP and into the myocardium (MC). Then, the introducer 62 is retracted from the sleeve access lumen 36.

Pacing and sensing threshold tests are conducted in the conventional manner to determine that the implantation site is suitable. If the thresholds are acceptable, the suction S is then discontinued, and the trocar sleeve 34 can be removed from the incision 20 of FIG. 1. The lead body and proximal connector of the lead 60 can then be routed subcutaneously in a conventional manner to the site of implantation of an to complete the implantation of the cardiac pacemaker in the patient's body.

Figure 10:
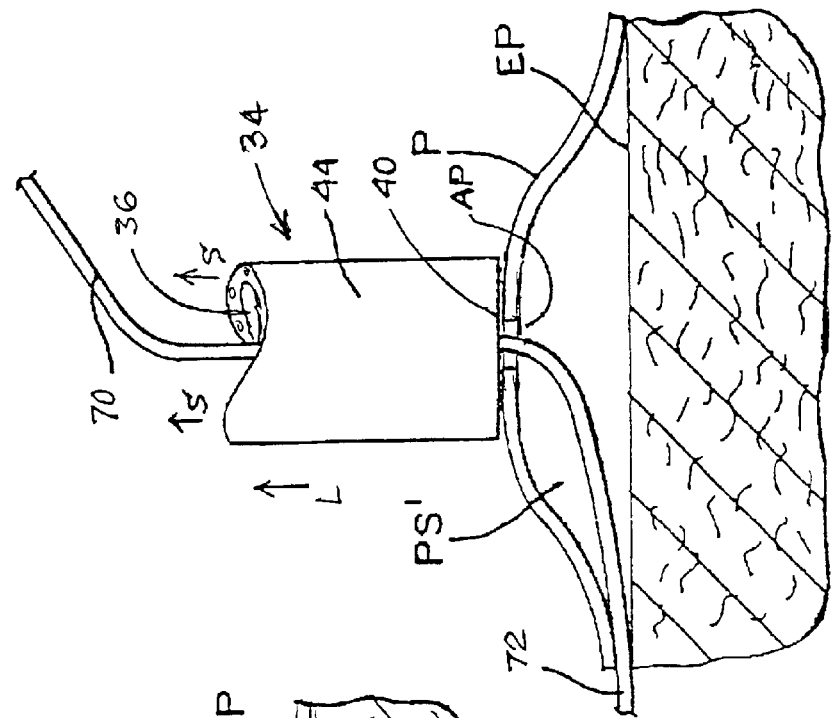
FIG. 10 is a schematic illustration of the insertion of a further medical device through the sleeve access lumen into the pericardial space and laterally along the epicardium to a selected lateral site or the pericardial space during the application of suction from the plurality of suction ports to the epicardium enabling lifting of the epicardium to expand the pericardial space.

FIG. 10 schematically illustrates the insertion of a further elongated medical device 70 comprising an instrument, catheter, or medical electrical lead cardiac pacing lead, etc., through the sleeve access lumen 36 into the expanded pericardial space PS' and advancement of the instrument distal tip 72 laterally along the epicardium EP to a selected lateral site of the expanded pericardial space PS'.

Suction S and lift L are applied as described above to expand the pericardial space PS' during the lateral advancement of the instrument distal tip 72. The lateral advancement of the further elongated medical device 70 is facilitated by inserting the trocar 22 through incision 20 at an oblique angle to the pericardium P, which is likely to be the case most of the time. The oblique approach can be facilitated by providing an angled sleeve distal end 40' as shown in FIG. 11 that is rotated in incision 20 until the angled sleeve distal end 40' optimally engages against the outer surface of pericardium P.

The lateral advancement of the further elongated medical device 70 can also be facilitated by use of an introducer guide wire or catheter having a deflectable distal tip or a curved distal segment that is straightened when inserted into the sleeve access lumen 36. The curve in the distal end or segment is restored when the distal end or segment is advanced out of the distal end opening of the sleeve access lumen 36 and into the expanded pericardial space PS'.

Figure 11:
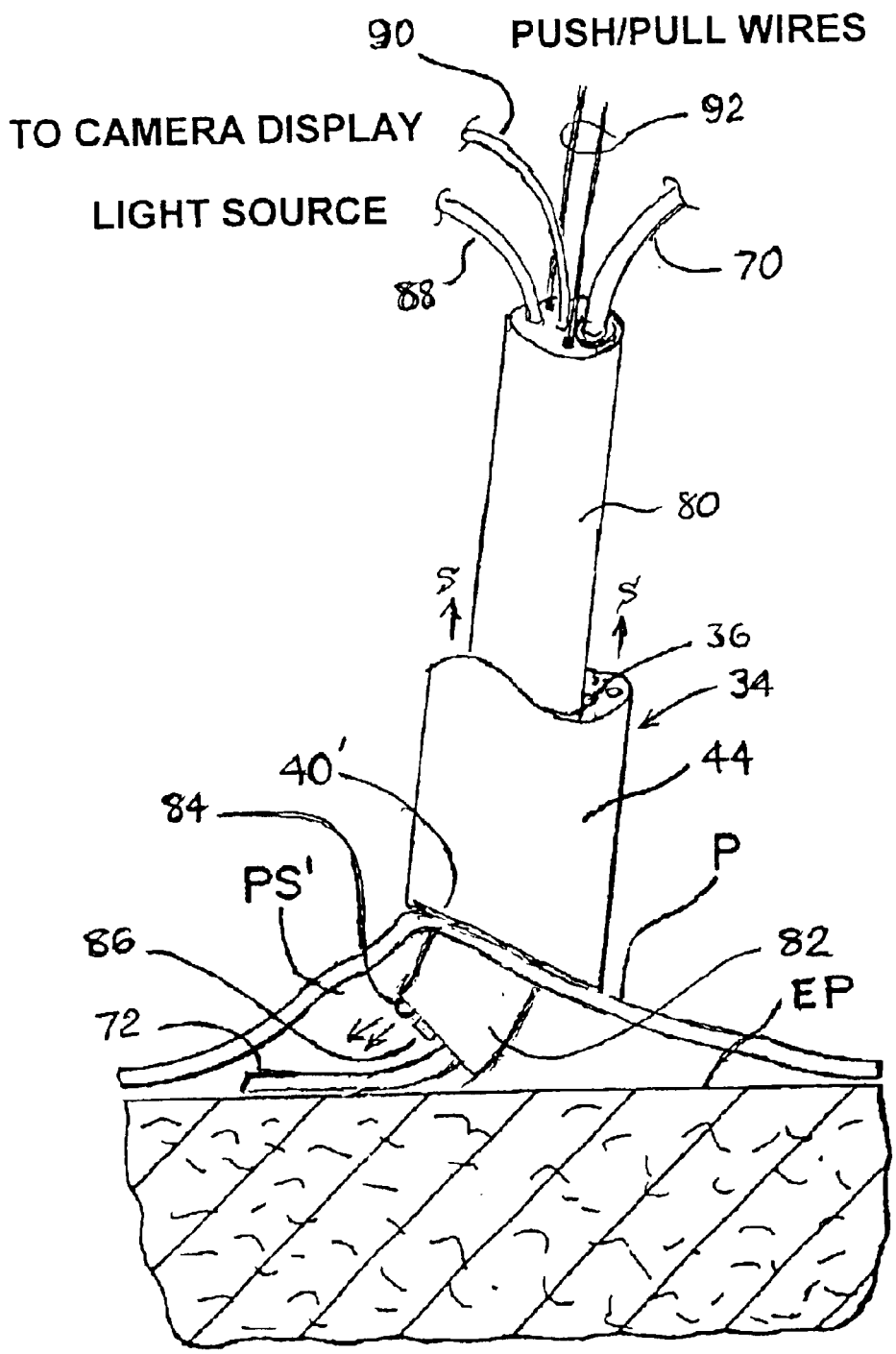
FIG. 11 is a schematic illustration of the insertion of a deflectable tip endoscope and light source for visualizing the pericardial space laterally having an integral endoscope lumen through which a medical device is advanced into the pericardial space during the application of suction from the plurality of suction ports to the epicardium enabling lifting of the epicardium to expand the pericardial space.

FIG. 11 schematically illustrates the incorporation of these features into an endoscope 80 advanced through the sleeve access lumen 36 and having a deflectable distal segment 82 and an introducer lumen through which the elongated medical device can be introduced into the expanded pericardial space PS'. The endoscope 80 can incorporate any of the known deflectable tip control mechanisms, an introducer lumen, a lamp or light pipe distal end 84 for illuminating the expanded pericardial space PS', and an image capture device 86, e.g., a digital camera or a light pipe distal end extending to an external image display. The external light source comprises either a power supply or a lamp that is coupled either through power conductors or a light pipe, respectively, 88 to the either the lamp or light pipe distal end, respectively, 84. The external visual display is either coupled optically to the light pipe or through a set of conductors 90 powering and receiving data from the image capture device 86.

In use, the elongated medical device 70 is inserted into the introducer lumen, the endoscope 80 is inserted into the sleeve access lumen 36, and the right angle or angled trocar sleeve distal end 40 or 40' is advanced and oriented against the pericardium P. Suction S and lift L are applied as described above, and the expanded pericardial space PS' is created.

The deflectable distal segment 82 of the endoscope 80 is then advanced into the expanded pericardial space PS'. Light is emitted into the expanded pericardial space PS' by lamp or light pipe distal end 84, and the illuminated area is displayed via the image capture device 86.

The distal segment 82 is preferably deflectable so that it can be deflected to orient the introducer lumen distal end opening laterally through movement of the push-pull wires at the endoscope proximal end while observing the illuminated area of the expanded pericardial space PS'. Once the desired orientation is achieved, the distal end 72 of the elongated medical device 70 is advanced laterally in the expanded pericardial space PS' and further in the unexpanded pericardial space PS to a desired site.

It should be understood that certain of the features of the endoscope 82 can be incorporated into the sleeve wall.

Figure 12:
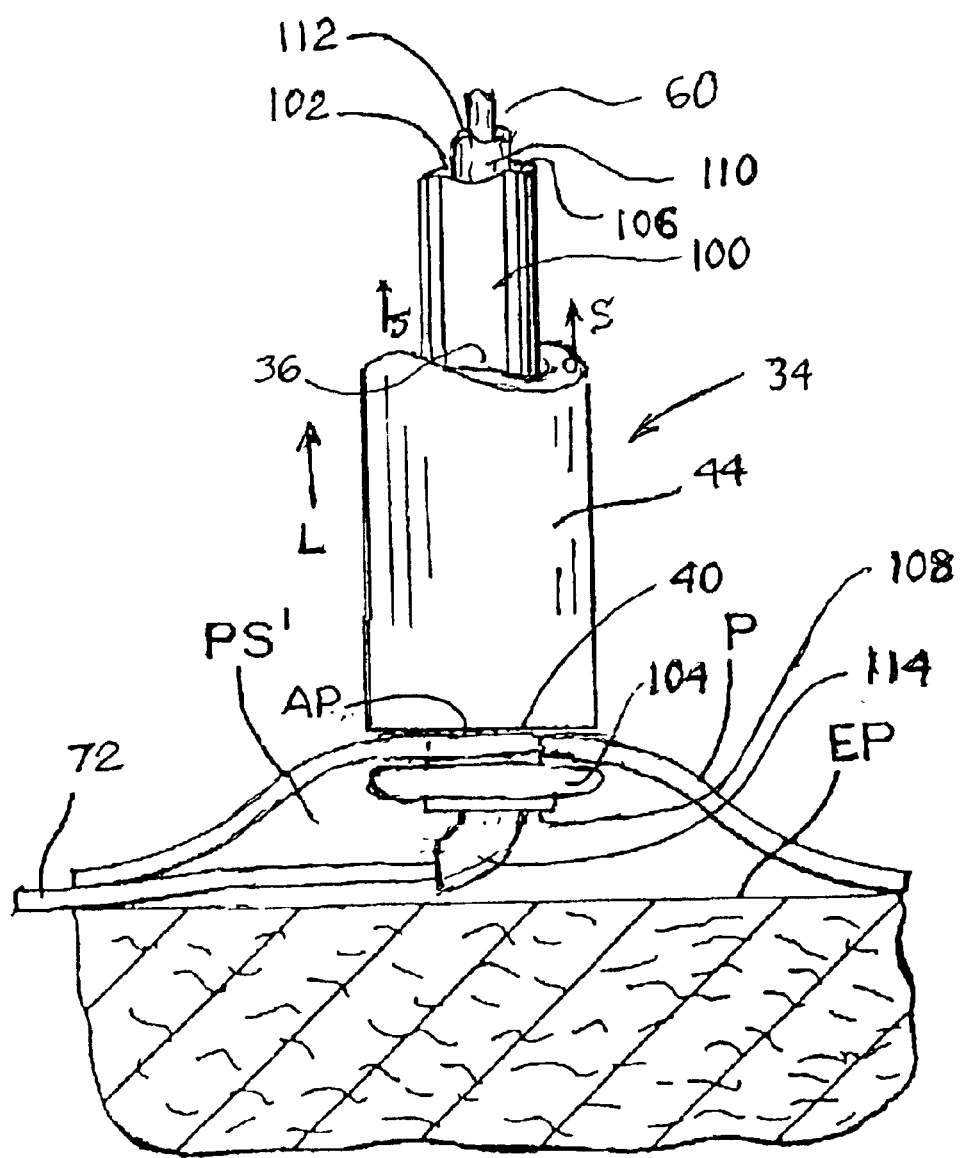
FIG. 12 is a schematic illustration of the insertion of a retractor, particularly a balloon catheter, through the sleeve access lumen into the expanded pericardial space to reinforce the suction force, and the insertion of a medical device through a precurved introducer.

It may also be desirable to introduce a retention mechanism into the expanded pericardial space PS' that reinforces the attachment of the sleeve distal end 40 or 40' to the pericardium P and inhibits retraction of the sleeve distal end 40 away from the pericardium P. FIG. 12 is a schematic illustration of the insertion of a retractor, particularly a balloon (or mechanical fixation) catheter 100, through the sleeve access lumen 36 into the expanded pericardial space PS' to reinforce the suction force. A precurved introducer 110 is also illustrated introduced through the balloon catheter lumen 102. The elongated medical device 70 is introduced through the introducer lumen 112. It will be understood that the precurved introducer 110 can be eliminated and that a retraction mechanism can be employed with or incorporated into the endoscope 80 or lead delivery introducer 64. The balloon 104 is adapted to be inflated to apply retraction force against the inner surface of the pericardium P and press the pericardium P against the plurality of suction ports illustrated in FIGS. 3–5 and described above. The suction S can also be discontinued if the inflated balloon diameter is sufficiently large to inhibit retraction of the balloon 104 through the access perforation AP. The balloon 104 is inflated and deflated through an inflation/deflation lumen 106 in the sidewall of the balloon catheter 100 in the conventional manner.

In use, the introducer distal segment 114 is straightened and inserted into the balloon catheter lumen 102, and the introducer 110 is advanced toward the balloon catheter distal end 108. The elongated medical device 70 is inserted into the proximal end opening of the introducer lumen 112 and advanced to the introducer distal end. The assembly of the balloon catheter 100, the introducer 110, and the elongated medical device 70 is inserted and advanced through the sleeve access lumen 36, and the right angle or angled trocar sleeve distal end 40 or 40' is advanced and oriented against the pericardium P.

The balloon 104 is then advanced into the expanded pericardial space PS' and inflated as suction S and lift L are applied as described above, and the expanded pericardial space PS' is created. The curve in the introducer distal segment 114 is restored as it is advanced out of the balloon catheter lumen 102. The introducer 110 and elongated medical device 70 can be rotated within the balloon catheter lumen 102 to aim the elongated medical device in the desired direction. Then, the elongated medical device distal end 72 is advanced out of the introducer lumen 112 and laterally in the expanded pericardial space PS' and further in the unexpanded pericardial space PS to a desired site.

Another retention mechanism that can be substituted for the balloon 104 comprises expandable cages or fingers that can be expanded outward and pulled back inward through use of push-pull wires. Such an expandable cage retention mechanism is disclosed, for example, in U.S. Pat. No. 5,402,772.

Or the retraction mechanism comprises flexible, pliant tines formed of polyurethane or silicone rubber or shape memory alloy and mounted near the catheter distal end to extend outward of the catheter sidewall when located in the pericardial space PS'. Such tines are adapted to readily fold inward during advancement of the catheter distal end through the access perforation AP but resist retraction back out through the access perforation AP unless the catheter proximal end is retracted with sufficient force to fold the tines inward. Suitable tine retention mechanisms are disclosed, for example, in U.S. Pat. No. 5,300,107.

Conclusion

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A method for accessing an anatomic space within the body between an inner tissue layer and an outer tissue layer having an outer tissue layer outer surface comprising:

applying the distal end of a tubular access sleeve having a sleeve wall extending between a sleeve proximal end and a sleeve distal end and surrounding a sleeve access lumen extending between a sleeve access lumen proximal end opening and a sleeve access lumen distal end opening, the sleeve wall supporting a plurality of suction ports arrayed around the sleeve access lumen distal end opening against the outer surface of the outer tissue layer;

applying suction through the plurality of suction ports to a plurality of portions of the outer tissue layer;

introducing a perforation instrument through the sleeve access lumen to the outer surface of the outer tissue layer; and perforating the outer tissue layer to form an access perforation into the anatomic space while the applied suction stabilizes the outer tissue layer, whereby further treatment drugs and devices can be introduced into the anatomic space through the sleeve access lumen.

2. The method of claim 1, further comprising the step of drawing the access sleeve proximally to raise the outer tissue layer overlying the anatomic space and to enlarge the anatomic space.

3. The method of claim 1, further comprising the steps of:

withdrawing the perforation instrument from the sleeve access lumen; and introducing a medical device through the sleeve access lumen and the access perforation and into the anatomic space.

4. The method of claim 1, wherein the perforating step further comprises:

introducing a guidewire having a perforating distal tip through the sleeve access lumen; and advancing the perforating distal tip through the outer tissue layer, whereby the guidewire is adapted to enable advancement of a medical device over the guidewire through the access perforation and into the anatomic space.

5. The method of claim 1, further comprising the steps of:

withdrawing the perforation instrument from the sleeve access lumen;

introducing a guiding catheter having a catheter lumen extending between a catheter proximal end and a catheter distal end through the sleeve access lumen and the access perforation to dispose the catheter distal end in the anatomic space; and introducing a medical device through the catheter lumen and into the anatomic space.

6. The method of claim 1, further comprising the steps of:

withdrawing the perforation instrument from the sleeve access lumen;

introducing an endoscope having an introducer lumen extending between an endoscope proximal end and an endoscope distal end through the sleeve access lumen and the access perforation to dispose the endoscope distal end in the anatomic space, the endoscope having a light emitter that emits light at the endoscope distal end and an image capture device, operating the light emitter to illuminate the anatomic space;

introducing a medical device through the introducer lumen and into the anatomic space; and operating the image capture device to view the illuminated anatomic space and medical device.

7. The method of claim 1, further comprising the steps of:

withdrawing the perforation instrument from the sleeve access lumen;

introducing a guiding catheter having a catheter lumen extending between a catheter proximal end and a catheter distal end through the sleeve access lumen and the access perforation to dispose the catheter distal end in the anatomic space, laterally advancing a catheter distal end segment of the guiding catheter in a selected direction within the anatomic space; and introducing a medical device through the catheter lumen and into the anatomic space to extend laterally in the selected direction.

8. The method of claim 1, further comprising the steps of:

withdrawing the perforation instrument from the sleeve access lumen;

introducing an endoscope having an introducer lumen extending between an endoscope proximal end and an endoscope distal end through the sleeve access lumen and the access perforation to dispose the endoscope distal end in the anatomic space, the endoscope having a light emitter that emits light at the endoscope distal end and an image capture device, laterally advancing an endoscope distal end segment of the endoscope in a selected direction within the anatomic space;

operating the light emitter to illuminate the anatomic space;

introducing a medical device through the introducer lumen and laterally into the anatomic space in the selected direction; and operating the image capture device to view the illuminated anatomic space and medical device.

9. The method of claim 1, further comprising the steps of:

introducing a retention device through the sleeve access lumen and into the anatomic space; and deploying the retention device in the anatomic space to bear against an interior surface of the outer tissue layer to inhibit retraction of the sleeve distal end from the exterior surface of the outer tissue layer.

10. The method of claim 1, further comprising the steps of:

introducing a retention catheter having a catheter lumen extending between a catheter proximal end and a catheter distal end through the sleeve access lumen and the access perforation to dispose the catheter distal end in the anatomic space, the retention catheter having a retention mechanism at the retention catheter distal end;

deploying the retention mechanism in the anatomic space to bear against an interior surface of the outer tissue layer; and introducing a medical device through the catheter lumen and into the anatomic space.

11. The method of claim 1, further comprising the steps of:

introducing a retention catheter having a catheter lumen extending between a catheter proximal end and a catheter distal end through the sleeve access lumen and the access perforation to dispose the catheter distal end in the anatomic space, the retention catheter having a retention mechanism at the retention catheter distal end;

deploying the retention mechanism in the anatomic space to bear against an interior surface of the outer tissue layer;

laterally advancing a catheter distal end segment of the retention catheter in a selected direction within the anatomic space; and introducing a medical device through the catheter lumen and into the anatomic space to extend laterally in the selected direction.

12. The method of claim 1, further comprising the steps of:

withdrawing the perforation instrument from the sleeve access lumen;

introducing an electrical medical lead extending between a lead proximal end and a lead distal end having a distal electrode and a fixation mechanism at the lead distal end through the sleeve access lumen and the access perforation to dispose the distal electrode and fixation mechanism in the anatomic space; and fixing the fixation mechanism to the interior tissue layer.

13. The method of claim 1, wherein the step of applying the sleeve distal end to the outer tissue layer further comprise:

inserting a tissue penetrating rod through the sleeve access lumen to form a two-piece trocar;

passing the trocar through body tissue to dispose the sleeve distal end within a body cavity;

removing the tissue penetrating rod from the sleeve access lumen; and advancing the sleeve distal end against the outer surface of the outer tissue layer.

14. A system for accessing an anatomic space within the body between an inner tissue layer and an outer tissue layer having an outer tissue layer outer surface comprising:

a tubular access sleeve having a sleeve wall extending between a sleeve proximal end and a sleeve distal end and surrounding a sleeve access lumen extending between a sleeve access lumen proximal end opening and a sleeve access lumen distal end opening, the sleeve wall supporting a plurality of suction ports at the sleeve distal end arrayed around the sleeve access lumen distal end opening adapted to be applied against the outer surface of the outer tissue layer, a suction manifold adapted to be coupled to a vacuum source, and at least one sleeve lumen extending from the suction manifold to the sleeve suction ports to enable suction of a portion of the outer tissue layer against each suction port enabling the application of lift to the sleeve proximal end to raise the outer tissue layer overlying the anatomic space and to enlarge the anatomic space; and a perforation instrument adapted to be introduced though the sleeve access lumen to the outer surface of the outer tissue layer to form an access perforation into the anatomic space while the applied suction stabilizes the outer tissue layer, whereby further treatment drugs and devices can be introduced into the anatomic space through the sleeve access lumen.

15. The system of claim 14, wherein the access sleeve comprises a trocar sleeve and further comprising a tissue penetrating rod adapted to be fitted through the access sleeve lumen to form a two-piece trocar adapted to be passed through body tissue into a body cavity and to be removed to leave the access sleeve in position to access the outer tissue layer through the sleeve access lumen.

16. The system of claim 14, wherein the plurality of suction ports are substantially flush with the sleeve distal end.

17. The system of claim 14, wherein the plurality of suction ports extend distally from the sleeve distal end.

18. The system of claim 14, wherein the access sleeve has a sleeve wall axis and the sleeve distal end in which the plurality of suction ports is formed is at an acute angle to the sleeve wall axis.

19. The system of claim 14, wherein the access sleeve has a sleeve wall axis and the sleeve distal end in which the plurality of suction ports is formed is substantially normal to the sleeve wall axis.

20. The system of claim 14, wherein the perforation instrument further comprises a guidewire having a perforating distal tip adapted to be advanced through the outer tissue layer, whereby the guidewire is adapted to enable advancement of a medical device over the guidewire through the access perforation and into the anatomic space.

21. The system of claim 14, further comprising a guiding catheter having a catheter lumen extending between a catheter proximal end and a catheter distal end, the guiding catheter sized to be advanced through the sleeve access lumen and the access perforation to dispose the catheter distal end in the anatomic space to enable introduction of a medical device through the catheter lumen and into the anatomic space.

22. The system of claim 14, further comprising an endoscope having an introducer lumen extending between an endoscope proximal end and an endoscope distal end through which a medical device is adapted to be advanced into the anatomic space, the endoscope having a light emitter that emits light at the endoscope distal end to illuminate the anatomic space and medical device, and an image capture device to view the illuminated anatomic space and medical device, the endoscope sized to be advanced through the sleeve access lumen and the access perforation to dispose the endoscope distal end in the anatomic space.

23. The system of claim 22, wherein the endoscope further comprises a laterally deflectable endoscope distal end segment and means for laterally deflecting the endoscope distal end segment to facilitate advancement of the medical device through the endoscope lumen and laterally within the anatomic space.

24. The system of claim 14, further comprising a guiding catheter having a catheter lumen extending between a catheter proximal end and a catheter distal end through which a medical device is adapted to be advanced into the anatomic space, the guiding catheter sized to be advanced through the sleeve access lumen and the access perforation to dispose the catheter distal end within the anatomic space.

25. The system of claim 24, wherein the guiding catheter further comprises a laterally deflectable distal end segment and means for laterally deflecting the distal end segment to facilitate advancement of the medical device through the catheter lumen and laterally within the anatomic space.

26. The system of claim 14, further comprising a retention device adapted to be advanced through the sleeve access lumen and into the anatomic space and deployed in the anatomic space to bear against an interior surface of the outer tissue layer to inhibit retraction of the sleeve distal end from the exterior surface of the outer tissue layer.

27. The system of claim 14, further comprising a retention catheter having a catheter lumen extending between a catheter proximal end and a catheter distal end and sized to be advanced through the sleeve access lumen and the access perforation to dispose the catheter distal end in the anatomic space, the retention catheter further having a retention mechanism at the retention catheter distal end adapted to be deployed in the anatomic space to bear against an interior surface of the outer tissue layer to inhibit retraction of the sleeve distal end from the exterior surface of the outer tissue layer.

28. The system of claim 27, wherein the retention mechanism comprises an inflatable balloon coupled with an inflation/deflation lumen of the retention catheter, the balloon adapted to be deflated during passage of the retention catheter through the sleeve access lumen and inflated within the anatomic space.

29. The system of claim 27, wherein the retention mechanism comprises expandable cages or fingers adapted to be restrained inward during passage of the retention catheter through the sleeve access lumen and expanded outward within the anatomic space through use of push-pull wires.

30. The system of claim 27, wherein the retention mechanism comprises flexible, pliant tines mounted near the catheter distal end adapted to be restrained inward during passage of the retention catheter through the sleeve access lumen and to extend outward of the catheter sidewall when located in the pericardial space to resist retraction back out through the access perforation unless the catheter proximal end is retracted with sufficient force to fold the tines inward.

31. The system of claim 27, wherein the retention catheter comprises a retention catheter lumen extending between a catheter proximal end and a catheter distal end through which a medical device is adapted to be advanced into the anatomic space.

32. The system of claim 27, wherein the retention catheter further comprises:
   a retention catheter lumen extending between a catheter proximal end and a catheter distal end through which a medical device is adapted to be advanced into the anatomic space;
   a laterally deflectable distal end segment; and
   means for laterally deflecting the distal end segment to facilitate advancement of the medical device through the retention catheter lumen and laterally within the anatomic space.

33. The system of claim 14, further comprising
   an electrical medical lead extending between a lead proximal end and a lead distal end having a distal electrode and a fixation mechanism at the lead distal end, the electrical medical lead adapted to be introduced through the sleeve access lumen and the access perforation to dispose the distal electrode and fixation mechanism in the anatomic space; and
   means for fixing the fixation mechanism to the interior tissue layer.

* * * * *